(12) United States Patent
Parvulescu et al.

(10) Patent No.: US 6,404,984 B1
(45) Date of Patent: *Jun. 11, 2002

(54) LIGHTED CAMERA FOR DENTAL EXAMINATIONS AND METHOD OF USING THE SAME

(75) Inventors: Adrian Parvulescu, Fish's Eddy, NY (US); John M. Van Ryzin, Madison, NJ (US)

(73) Assignees: Sony Corporation, Tokyo (JP); Sony Electronics, Park Ridge, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/196,356

(22) Filed: Nov. 19, 1998

(51) Int. Cl.[7] ................................................. G03B 29/00
(52) U.S. Cl. ........................... 396/16; 396/199; 348/66; 348/68
(58) Field of Search ............................. 396/14, 16, 19, 396/199; 348/66, 68

(56) References Cited

U.S. PATENT DOCUMENTS

| | | | | |
|---|---|---|---|---|
| 3,812,505 A | * | 5/1974 | Elliott | 396/16 |
| 4,716,465 A | * | 12/1987 | Meyer | 348/211 |
| 5,010,412 A | * | 4/1991 | Garriss | 396/199 |
| 5,454,022 A | * | 9/1995 | Lee et al. | 378/98.8 |
| 5,487,661 A | * | 1/1996 | Peithman | 433/29 |
| 5,527,261 A | * | 6/1996 | Monroe et al. | |
| 5,555,019 A | * | 9/1996 | Dole | 348/148 |
| 5,671,158 A | * | 9/1997 | Fournier et al. | 364/514 |
| 5,771,067 A | * | 6/1998 | Williams et al. | 348/66 |
| 5,908,295 A | * | 6/1999 | Kawata | 433/29 |
| 5,926,262 A | * | 7/1999 | Jung et al. | |
| 6,002,424 A | * | 12/1999 | Rapa et al. | |

* cited by examiner

*Primary Examiner*—David M. Gray
(74) *Attorney, Agent, or Firm*—Ronald P. Kananen, Esq.; Rader, Fishman & Grauer, PLLC

(57) ABSTRACT

A self-contained dental camera uses white diodes to provide sufficient illumination for dental imaging without unduly depleting battery power. The illuminated dental work is imaged by a camera, preferably a CCD, and the resulting video signal is transmitted to a base station for display on a monitor. The camera unit may be disposed in a holder on a base station to recharge the battery.

12 Claims, 2 Drawing Sheets

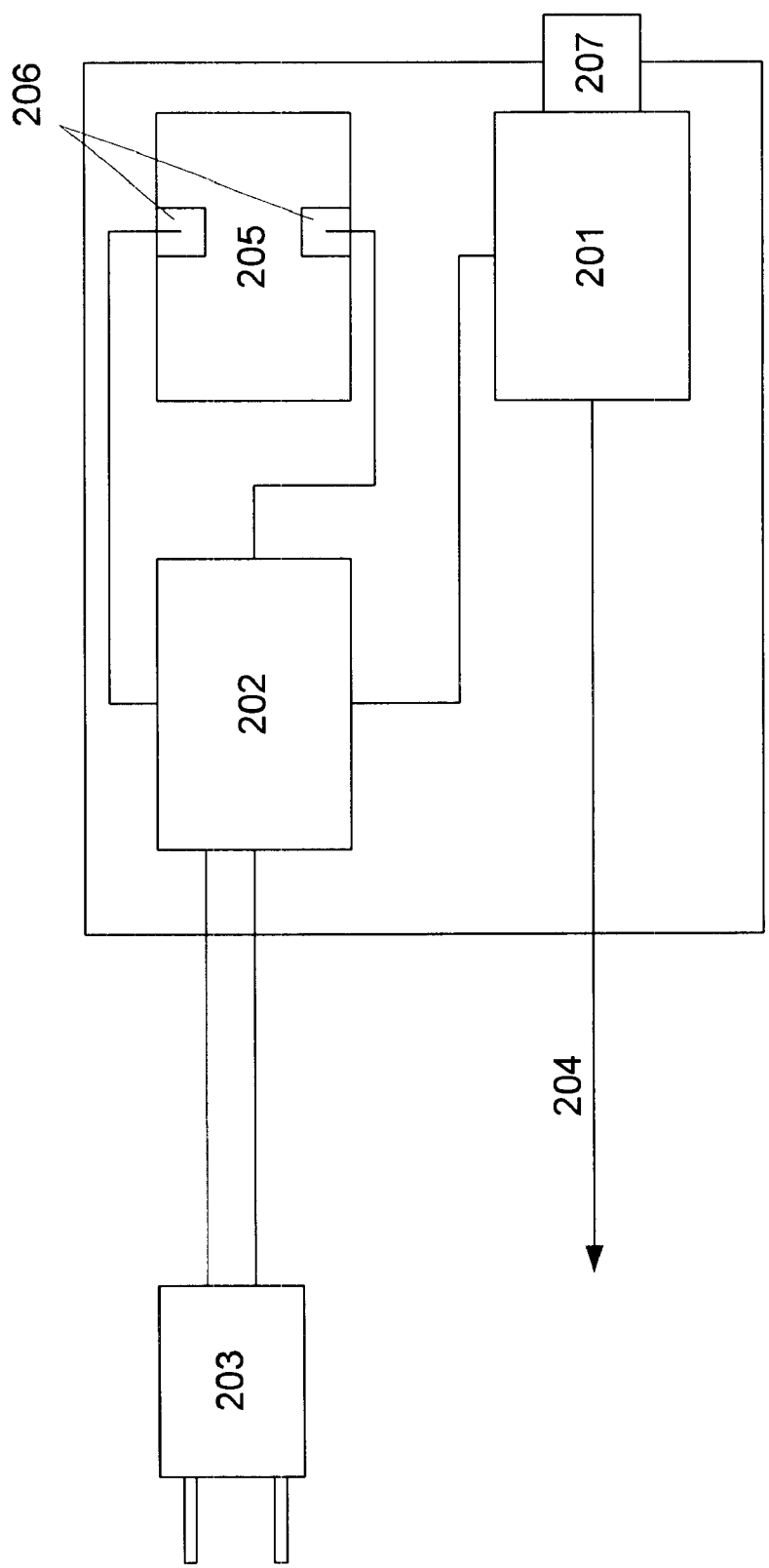

LIGHTED CAMERA FOR DENTAL EXAMINATIONS AND METHOD OF USING THE SAME

FIELD OF THE INVENTION

The present invention relates to the field of dental examinations. Specifically, the present invention relates to a lighted camera for oral examinations and a method of using the same.

BACKGROUND OF THE INVENTION

Detailed dental examinations are frequently conducted using a small camera connected to a monitor. The camera, typically a charged coupled device ("CCD"), photographs the dental work of the patient. The enlarged images from the camera are displayed on a connected monitor. The images can then be reviewed by the dentist, orthodontist, oral surgeon or other dental care provider to better diagnose the condition of the patient for purposes of treating that patient.

Conventionally, the light source for the CCD camera consists of a fiber optic cable tethered to a standard light bulb. The fiber optic cable delivers the light of the light bulb to the site in the patient's mouth being imaged by the CCD camera.

An electrical connection between the CCD camera and a display monitor can be conveniently provided in conjunction with the fiber optic cable. For example, the fiber optic cable and the electrical connection between camera and monitor may be commonly sheathed as a single cable or tether.

The principal problem with this arrangement is the unwieldy cable that results between the camera unit and the base unit where the light bulb is located. The user must at all times be concerned with the length restriction of the cable and the placement of the cable with regard to both the patient and other dental equipment in the area.

Clearly it would be a tremendous advantage in this field if the cable between the camera unit and the base unit could be eliminated. However, this would require that a relatively powerful light source be disposed on the camera unit itself. The problem with such an arrangement is the power consumption requirement of the light source. Heretofore, no arrangement has been proposed for a self-contained camera unit capable of providing power for both the camera and a light source which is capable of properly illuminating the patient's dental work for a sufficient and reasonable length of time.

Accordingly, there is a need in the art for a tether-less camera unit for dental examinations which includes a light source with power sufficient to illuminate the patient's dental work as needed for imaging during a dental examination.

SUMMARY OF THE INVENTION

It is an object of the present invention to meet the above-described needs and others. Specifically, it is an object of the present invention to provide a tether-less, wireless camera unit which includes a light source with power sufficient to illuminate the patient's dental work throughout the course of a dental examination.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve these stated and other objects, the present invention may be as embodied and described as a dental imaging system including at least one white diode for illuminating a portion of dental work to be imaged; and a camera for imaging the illuminated portion of dental work. Preferably, the system includes a plurality of white diodes arranged in a ring around a lens of the camera. The camera may be, for example, a CCD, and the system may include an optical coupler for guiding light from the lens to the camera.

The system may transmit video signals to a monitor over a wire connection to the monitor. Alternatively, the system of the present invention may include a wireless transmitter for wirelessly transmitting a video signal from the camera to the monitor. The transmitter may be a radio signal transmitter, but is preferably an infra-red optical signal transmitter. A base unit of the system includes a receiver for receiving the video signal from the camera and communicating the video signal to the monitor where it can be used by a dental practitioner.

A battery is used for powering the white diode (or diodes), the camera and, if present, the transmitter. Preferably, the white diode(s), the camera and the battery are mounted to a common housing as a camera unit.

Terminals may be provided on the exterior of the housing which are electrically connected to the battery. The base unit may then include a holder for the camera unit. Within the holder are electrical pads which contact the terminals when the camera unit is held in the holder allowing the base unit to recharge the battery.

The present invention also encompasses the method inherent in constructing and using the dental imaging system described above. Specifically, the present invention includes a method of providing dental imaging by the steps of illuminating a portion of dental work to be imaged with at least one white diode; and imaging the illuminated portion of dental work with a camera.

As before, the step of illuminating is preferably accomplished with a plurality of white diodes arranged in a ring around a lens of the camera. The method includes the step of powering the at least one white diode and the camera with a battery.

In order to realize the advantages of the present invention by eliminating the conventional tether between a dental camera and a base unit, the method of the present invention may include the steps of wirelessly transmitting a video signal from the camera with a transmitter; receiving the video signal from the transmitter with a receiver disposed in a base unit; and communicating the video signal to a monitor.

As above, the method of the present invention includes powering the at least one white diode, the camera and the transmitter with a battery. In order to maintain battery power, the method includes the steps of mounting the at least one white diode, the camera and the battery to a common housing as a camera unit; providing terminals on the housing which are electrically connected to the battery; holding the camera unit in a holder of a base unit; electrically contacting the terminals with electrical pads in the holder; and recharging the battery through the contact between the terminals and the pads.

BRIEF DESCRIPTION OF THE DRAWINGS

The accompanying drawings illustrate the present invention and are a part of the specification. Together with the following description, the drawings demonstrate and explain the principles of the present invention.

FIG. 2 is a diagram of a base unit according to the principles of the present invention for the camera unit of FIG. 1.

DETAILED DESCRIPTION OF THE PREFERRED EMBODIMENTS

Figure 1:
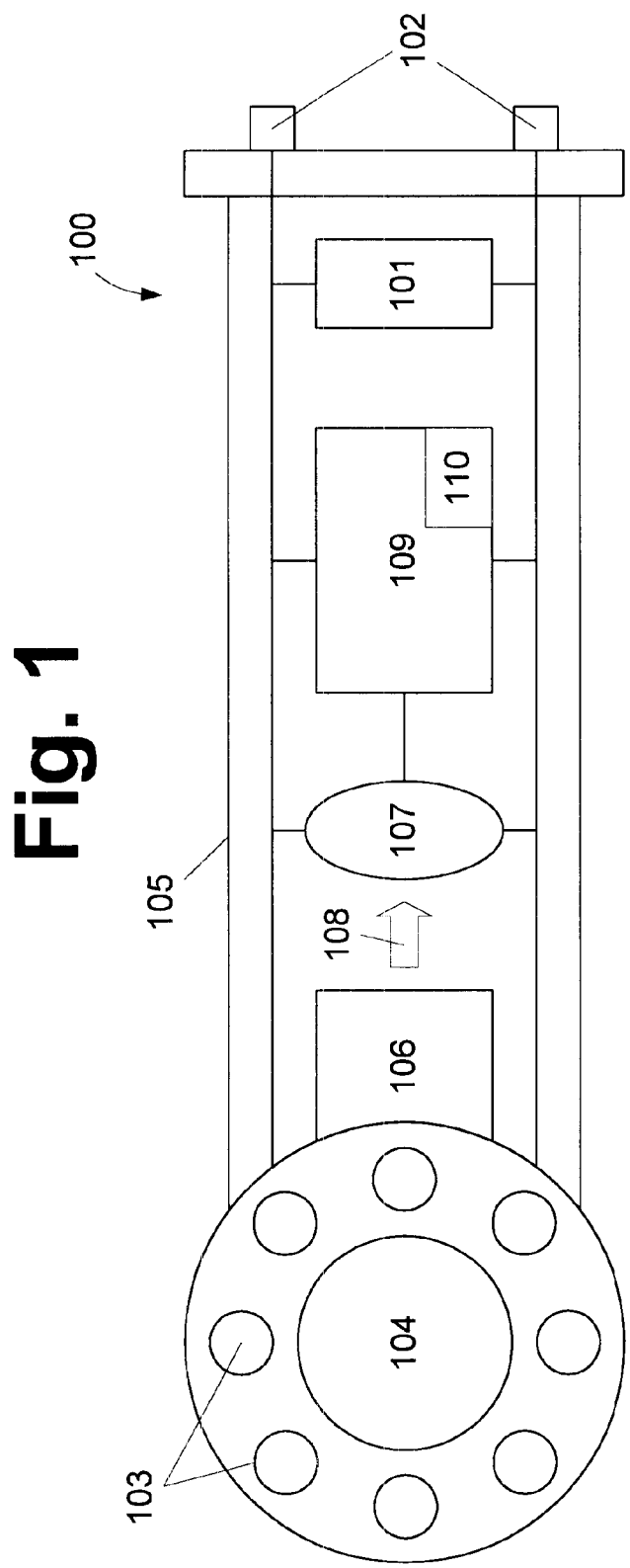
FIG. 1 is diagram of a self-contained, tether-less dental camera unit according to the principles of the present invention.

Using the drawings, the preferred embodiments of the present invention will now be explained. FIG. 1 illustrates a self-contained camera unit according to the principles of the present invention.

Some of the principal problems of the prior art discussed above are overcome in the present invention by the use of white diodes 103. It has been discovered that these diodes 103 are able to provide sufficient light for conducting dental examinations with a CCD camera 107, but have sufficiently low power requirements that a battery 101 can provide the required power for a sufficient and reasonable period of time.

As shown in FIG. 1, a plurality of white diodes 103 are preferably arranged in a ring on the head of a self-contained dental camera 100. At the center of the ring of diodes 103 is a lens 104. The ring of white diodes 103 provide the required light at the site of a patient's dental work that is to be examined. Once the site is illuminated by the diodes 103, the site is imaged through lens 104.

The lens 104 is optically coupled with a light guide element 106 which directs the light 108 from the lens 104 to the CCD camera 107. The light guide 106 may be any of a number of equivalent elements including, but not limited to, a mirror, an optical fiber or a wave guide. Any element capable of guiding the light 108 from the lens 104 to the CCD camera 107 is equivalent for purposes of the present invention. Alternatively, if the light path between the lens 104 and the CCD camera 107 is not bent or angled, the lens 104 may directly focus light on the CCD camera 107.

The CCD camera 107 may be connected to a base system (not shown) by a conventional wire tether in order to provide the video signal output by the camera 107 to a monitor (not shown) on which the video is displayed for used by a dental practitioner. However, the video signal output by the camera 107 may also be wirelessly transmitted by a wireless transmitter 109.

The transmitter 109 transmits the video signal to a receiver 201 (FIG. 2) so that the image from the camera 107 can be displayed on a monitor (not shown) for inspection by the dental practitioner using the camera unit 100. The transmitter 109 can be any of a number of wireless transmitters including, but not limited to, a radio frequency transmitter or an infrared optical transmitter. Any transmitter that can wirelessly send the video signal from the camera 107 to a base unit for display is equivalent for purposes of the present invention.

The white diodes 103, the CCD camera 107, and the transmitter 109 are powered by a battery 101 as shown in FIG. 1. The battery 101 is also connected to two electrical terminals 102 provided on the exterior of the camera unit 100. The terminals 102 can be used to connect the battery 101 to an outside power source to recharge the battery 101.

FIG. 2 illustrates a base station for use with the camera unit 100 of FIG. 1. The base unit of FIG. 2 includes a power regulator and charger 202. The power regulator 202 is powered by a conventional wall outlet (not shown) through a 120 V plug 203. The voltage rating of the plug 203 may be other than 120 V to accommodate the local standard voltage provided to wall outlets.

The power regulator 202 powers a receiver 201 that receives the video signal transmitted by the transmitter 109 of the camera unit 100. The receiver 201 will correspond to the type of transmitter 109 used in the camera unit 100. For example, the receiver 201 may be a radio receiver or an infra-red receiver.

While one purpose of the present invention is to eliminate the need for a physical connection between the camera unit and the base unit, it is not beyond the scope of the invention to include a physical wire connection between the camera unit 100 and the receiver 201 as described above. Accordingly, receiver 201 may have a port 207 to which a cable may be connected between a similar port 110 of the transmitter 109 and the receiver 201.

The receiver 201 also has a connection to a terminal 204 that is connected to a monitor (not shown). Through this connection, the receiver can display the video signal received from receiver 109 for the inspection of the dental practitioner using the camera unit 100.

The base unit of FIG. 2 also includes a holder 205 for the wireless camera unit 100 of FIG. 1. The holder 205 may receive and hold the camera unit 100. Moreover, the holder 205 includes two electrical contact pads 206 that correspond to the terminals 102 on the camera unit. When the camera unit 100 is placed in the holder 205, the terminals 102 are brought into contact with the pads 206 making an electrical connection. Through this connection, the power regulator 202 can recharge the battery 101 in the camera unit 100.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A dental imaging system comprising:
   a sensor for imaging dental work;
   a plurality of white diodes mounted on a head of said dental imaging system;
   a lens mounted on said head of said dental imaging system, said plurality of white diodes being arranged in a circular ring around said lens;
   an optical coupler positioned between said lens and said sensor, said optical coupler bending a path of light between said lens and said sensor;
   a transmitter for transmitting a video signal from said sensor, said transmitter transmitting said video signal both wirelessly and by cable;
   a battery for powering said plurality of white diodes, said sensor, and said transmitter; and
   a common housing for mounting, therein, said plurality of white diodes, said lens, said optical coupler, said sensor, said transmitter, and said battery.

2. A system as claimed in claim 1, wherein said sensor is a charge-coupled device.

3. A system as claimed in claim 1, further comprising a base unit comprising a receiver for receiving said video signal from said transmitter and communicating said video signal to a monitor.

4. A system as claimed in claim 1 further comprising:

terminals electrically connected to said battery; and a base unit comprising a holder for said camera, said holder including electrical pads which contact said terminals when said sensor is held in said holder allowing said base unit to recharge said battery.

5. A system as claimed in claim 1, wherein said transmitter is an infrared optical signal transmitter and said video signal is wirelessly transmitted as an infrared optical signal.

6. A system as claimed in claim 1, wherein said transmitter a radio frequency signal transmitter and said video signal is wirelessly transmitted as a radio frequency signal.

7. A method of providing dental imaging including the steps of:

illuminating a portion of dental work to be imaged with a plurality of white diodes, said plurality of white diodes being mounted on a head of a dental imaging system and arranged in a circular ring around a lens of a sensor;

coupling a path of light from said plurality of white diodes between a lens and said sensor, wherein said path of light is bent between said lens and said sensor, said lens being mounted on the head of a dental imaging system;

imaging said illuminated portion of dental work with said path of light by said sensor;

transmitting a video signal from said sensor with a transmitter, said transmitter transmitting said video signal both wirelessly and by cable;

mounting said plurality of white diodes, said lens, said optical coupler, said sensor, said transmitter, and said battery within a common housing; and powering said plurality of white diodes, said sensor and said transmitter with a battery.

8. A method as claimed in claim 7, wherein said sensor is a charge-coupled device.

9. A method as claimed in claim 7, further comprising:

receiving said video signal from said transmitter with a receiver disposed in a base unit; and communicating said video signal to a monitor.

10. A method as claimed in claim 7, further comprising:

providing terminals electrically connected to said battery;

holding said sensor in a holder of a base unit;

electrically contacting said terminals with electrical pads in said holder; and recharging said battery through said contact between said terminals and said pads.

11. A method as claimed in claim 7, wherein said transmitter an infrared optical signal transmitter and said video signal is wirelessly transmitted as an infrared optical signal.

12. A method as claimed in claim 7, wherein said transmitter a radio frequency signal transmitter and said video signal is wirelessly transmitted as a radio frequency signal.

* * * * *